United States Patent
Sanderson et al.

(10) Patent No.: US 10,576,101 B2
(45) Date of Patent: Mar. 3, 2020

(54) RONEPARSTAT COMBINED THERAPY OF MULTIPLE MYELOMA

(71) Applicants: Leadiant Biosciences SA, Mendrisio (CH); The UAB Research Foundation, Birmingham, AL (US)

(72) Inventors: Ralph D. Sanderson, Birmingham, AL (US); Vishnu Prakash C. Ramani, Birmingham, AL (US); Alessandro Noseda, Mendrisio (CH); Paola Barbieri, Mendrisio (CH)

(73) Assignees: Leadiant Biosciences SA, Mendrisio (CH); The UAB Research Foundation, Birmingham, AL (US)

( * ) Notice: Subject to any disclaimer, the term of this patent is extended or adjusted under 35 U.S.C. 154(b) by 0 days.

(21) Appl. No.: 15/556,183

(22) PCT Filed: Mar. 3, 2016

(86) PCT No.: PCT/IB2016/051196
§ 371 (c)(1),
(2) Date: Sep. 6, 2017

(87) PCT Pub. No.: WO2016/142814
PCT Pub. Date: Sep. 15, 2016

(65) Prior Publication Data
US 2018/0050061 A1 Feb. 22, 2018

Related U.S. Application Data

(60) Provisional application No. 62/129,221, filed on Mar. 6, 2015, provisional application No. 62/153,899, filed on Apr. 28, 2015.

(51) Int. Cl.
*A61K 31/727* (2006.01)
*A61K 31/198* (2006.01)
*A61K 38/05* (2006.01)
*A61K 38/07* (2006.01)

(52) U.S. Cl.
CPC .......... *A61K 31/727* (2013.01); *A61K 31/198* (2013.01); *A61K 38/05* (2013.01); *A61K 38/07* (2013.01); *A61K 2300/00* (2013.01)

(58) Field of Classification Search
CPC .... A61K 31/727; A61K 31/198; A61K 38/07; A61K 38/05; A61K 2300/00
USPC ........................................................ 435/325
See application file for complete search history.

(56) References Cited

U.S. PATENT DOCUMENTS

| 4,997,651 A | 3/1991 | Poole et al. |
| 2010/0009934 A1 | 1/2010 | Rickles et al. |

OTHER PUBLICATIONS

Hammond et al. The role of heparanase and sulfatases in the modification of heparan sulfate proteoglycans within the tumor microenvironment and opportunities for novel cancer therapeutics. Frontiers in Oncology/Molecular and Cellular Oncology, vol. 4, 195, p. 1-14, 2014. doi:10.3389/fonc.2014.00195 (Year: 2014).*
Berenson et al. Phase I/II Trial Assessing Bortezomib and Melphalan Combination Therapy for the Treatment of Patients With Relapsed or Refractory Multiple Myeloma. J Clin Oncol 24:937-944, 2006. (Year: 2006).*
Alkeran® (melphalan hydrochloride) for Injection. Updated Feb. 15, 2012. https://dailymed.nlm.nih.gov/dailymed/drugInfo.cfm?setid=9706e9a1-96ab-46b8-8846-32ee9d756b1d (Year: 2012).*
Stark, International Search Report and Written Opinion for PCT/IB2016/051196, dated Jul. 15, 2016.
Pisano et al., "The potential of heparanase as a therapeutic target in cancer" Biochem Pharmacol. May 1, 2014; 89 (1): 12-19.
Ritchie et al., "SST0001, a Chemically modified heparin, inhibits myeloma growth and angiogenesis via disruption of the heparanase/syndecan-1 axis" Clin. Cancer Res., 17 (6) Mar. 15, 2011.
Selby et al., "Multiple myeloma treated with high dose intravenous melphan." British Journal of Haematology, 1987, 66, 55-62.
Qin et al. "Proteasome inhibitors trigger NOXA-mediated apoptosis in melanoma and myeloma cells" Cancer Res. Jul. 15, 2005, 65 (14), 6282-6293.
Lonial et al., "Current advances in novel proteasome inhibitor-based approaches to the treatment of relapsed/refractory multiple myeloma" Oncology Supplements, Multiple Myeloma Oncology Journal, Nov. 11, 2017, p. 1-6.
Field-Smith et al., "Bortezomib (Velcade) in the treatment of multiple myeloma" Therapeutics and Clinical Risk Management, 2006, 2 (3), p. 271-278.
Jakubowiak, "Evolution of carfilzomib dose and schedule in patients with multiple myeloma: A historical overview." Cancer Treatment Reviews, v 40, n 6, p. 781-790, Year 2014.
Kapoor et al., "Bortezomib combination therapy in multiple myeloma" Conference Info: Seminars in Hematology, Jul. 1, 2012, v 49, n 3, p. 228-242.

\* cited by examiner

*Primary Examiner* — Yih-Horng Shiao
(74) *Attorney, Agent, or Firm* — Greer, Burns & Crain, Ltd.; Gregory P. Einhorn

(57) ABSTRACT

The present invention relates to roneparstat for use in a combined therapy for the treatment of multiple myeloma. In particular it has unexpectedly been found that the combined use of roneparstat with a proteasome inhibitor, in particular selected between bortezomib and carfilzomib or with melphalan improve efficacy in decreasing the overall tumor burden, especially showing synergism, with respect to the administration of each active ingredient alone.

22 Claims, 4 Drawing Sheets

RONEPARSTAT COMBINED THERAPY OF MULTIPLE MYELOMA

This application is a national phase application claiming benefit of priority under 35 U.S.C. § 371 to International (PCT) Patent Application serial number PCT/IB2016/051196, filed Mar. 3, 2016, which claims benefit of priority to U.S. provisional patent application Ser. No. 62/129,221, filed Mar. 6, 2015, and U.S. Ser. No. 62/153,899, filed Apr. 28, 2015. The aforementioned applications are expressly incorporated herein by reference in their entirety and for all purposes.

FIELD OF THE INVENTION

The present invention relates to roneparstat for use in a combined therapy for the treatment of multiple myeloma.

BACKGROUND OF THE INVENTION

Plasma cell myeloma (or multiple myeloma or MM) accounts for approximately 1.3% of neoplastic diseases and 17.9% of hematologic cancers (Globocan-EU28, 2012, see http://globocan.iarc.fr/Pages/fact_sheets_cancer.aspx). The median age at diagnosis is approximately 70 years; 37% of patients are younger than 65 years, 26% are between the ages of 65 and 74 years, and 37% are 75 years of age or older. Plasma cell myeloma (PCM) is slightly more common in men than in women and is twice as common in African-Americans compared to Caucasians.

PCM remains incurable despite conventional and high-dose chemotherapy.

Despite improvements in the therapeutic armamentarium, curative therapy does not exist, and all patients eventually experience relapse. The prognosis is particularly poor for patients with relapsed and refractory disease, with survival estimates ranging from 6 to 9 months. In addition to resistance to the currently available therapies, patients who progress failing multiple novel agents have limited treatment options, because of the presence of co-morbid conditions due to the primary disease or to prior therapies.

New, effective and well tolerated agents for the treatment of relapsed myeloma are therefore still needed.

In the 1960s, melphalan+prednisone (MP) therapy was introduced for the treatment of MM, which extended the median survival from approximately 1.5 years to 2 years. Since the late 1990s, high-dose melphalan therapy (200 mg/m$^2$) followed by autologous stem cell transplantation (ASCT) has been applied after induction therapy with vincristine+adriamycin+dexamethasone (VAD) in patients younger than 65 years of age, which resulted in the further improvement of survival to 5 years. Consequently, induction therapy+ASCT has been regarded as a standard therapy for younger patients with good health condition, and MP therapy was regarded as a standard of care for elderly patients of 65 years of age or older. Autologous hematopoietic stem cell transplantation (HSCT) involves the intravenous (IV) infusion of autologous stem cells to reestablish hematopoietic function in patients whose bone marrow or immune system is damaged or defective.

In the early phase of the 21st century, novel agents such as thalidomide, bortezomib, and lenalidomide have entered into clinical practice and become key drugs in the treatment of MM.

Bortezomib-based regimens are now used as induction therapy before ASCT in transplant-eligible patients, and MP+thalidomide, MP+bortezomib, and lenalidomide+dexamethasone are the widely used regimens for transplant-ineligible patients. Several clinical studies have shown an improvement of overall response rate and progression-free survival (PFS) in both transplant-eligible and transplant-ineligible patients by incorporating novel agents into anti-myeloma therapy. Multiple myeloma remains an incurable disease despite the availability of multiple treatments such as conventional and high-dose chemotherapy. The lack of available effective and safe therapies to treat resistant/relapsing tumors constitutes a critical and ongoing unmet medical need.

Proteasome inhibition has in fact assumed a central role in the management of MM, due to the effectiveness of this treatment strategy and a manageable safety profile.

Bortezomib is used at every stage of treatment for MM, from frontline combination therapy, to re-treatment for relapsed disease, therapy for refractory disease, and as induction, consolidation, and maintenance therapy before and after auto HSCT.

Bortezomib is a reversible inhibitor of the chymotrypsin-like activity of the 26S proteasome in mammalian cells. The 26S proteasome is a large protein complex that degrades ubiquitinated proteins. The ubiquitinproteasome pathway plays an essential role in regulating the intracellular concentration of specific proteins, thereby maintaining homeostasis within cells. Inhibition of the 26S proteasome prevents this targeted proteolysis, which can affect multiple signaling cascades within the cell. This disruption of normal homeostatic mechanisms can lead to cell death. Experiments have demonstrated that bortezomib is cytotoxic to a variety of cancer cell types in vitro. Bortezomib causes a delay in tumor growth in vivo in nonclinical tumor models, including multiple myeloma. Therefore, MM cells undergo apoptosis more readily when protein homeostasis is disrupted (Adams J., Nat. Rev. Cancer, 2004, 4, 349-360). This confers selectivity to these agents and a therapeutic index that is non-cell cycle specific (unlike cytotoxic chemotherapeutic agents, which affect all dividing cells and derive their selectivity from the fact that a larger fraction of the cancer cells are undergoing mitosis at any given time, compared to normal cells).

Bortezomib (VELCADE®) is a dipeptide boronic acid and chymotryptic site-selective inhibitor of the 20S proteasome. It has been approved in the U.S for the treatment of patients with multiple myeloma and for the treatment of patients with mantle cell lymphoma. It has been approved in Europe as monotherapy for the treatment of adult patients with progressive multiple myeloma who have received at least 1 prior therapy and who have already undergone or are unsuitable for bone marrow transplantation.

In combination with melphalan and prednisone, bortezomib is indicated for the treatment of adult patients with previously untreated multiple myeloma who are not eligible for high-dose chemotherapy with bone marrow transplant.

In multiple myeloma, complete clinical responses have been obtained in patients with otherwise refractory or rapidly advancing disease (Merin N M, Kelly K R. Pharmaceuticals (Basel). 2014 Dec. 24; 8(1):1-20).

The boron atom in bortezomib binds the catalytic site of the 26S proteasome with high affinity and specificity. In normal cells, the proteasome regulates protein expression and function by degradation of ubiquitinylated proteins, and also cleanses the cell of abnormal or misfolded proteins.

Carfilzomib (KYPROLIS™) is a tetrapeptide epoxyketone proteasome inhibitor that irreversibly binds to the N-terminal threonine-containing active sites of the 20S proteasome, the proteolytic core particle within the 26S proteasome. The chemical name for carfilzomib is (2S)—N—((S)-1-((S)-4-methyl-1-((R)-2-methyloxiran2-yl)-1-oxopentan-2-ylcarbamoyl)-2-phenylethyl)-2-((S)-2-(2-morpholinoacetamido)4-phenylbutanamido)-4-methylpentanamide.

Carfilzomib had antiproliferative and proapoptotic activities in vitro in solid and hematologic tumor cells. In animals, carfilzomib inhibited proteasome activity in blood and tissue and delayed tumor growth in models of multiple myeloma, hematologic, and solid tumors. Carfilzomib has been approved by US FDA for the treatment of patients with multiple myeloma who have received at least two prior therapies including bortezomib and an immunomodulatory agent and have demonstrated disease progression on or within 60 days of completion of the last therapy.

Proteasome inhibitors are currently studied for the treatment of relapsed/refractory multiple myeloma, see the review by Lonial and Boise, Oncology Journal, November 2011.

Melphalan (ALKERAN®, L-sarcolysin) is a chemotherapy drug belonging to the class of nitrogen mustard alkylating agents. An alkylating agent works by adding an alkyl group ($C_nH_{2n+1}$) to DNA. In particular it binds the alkyl group to the guanine base of DNA, at the number 7 nitrogen atom of the imidazole ring, thus producing linkages between strands of DNA. This chemical modification inhibits DNA synthesis and RNA synthesis, which are biological functions essential for the cells to survive. These chemical modifications therefore cause cytotoxicity in both dividing and non-dividing tumor cells.

Structurally melphalan is a phenylalanine derivative of mechlorethamine.

Roneparstat (proposed INN, previously also designated as [100]NA-RO.H or SST0001 or G4000) is a modified heparin derivative that is 100% N-desulphated, N-reacetylated and glycol split (Casu B et al., Pathophysiol Haemost Thromb, 2008; 36:195-20; Naggi A et al., J Biol Chem. 2005; 280:12103-13). These modifications abolish the anticoagulant activity at the doses expected to achieve a significant enzyme inhibition, while any possible residual anticoagulant activity in the high dose range is devoid of any clinical relevance, but enhance the inhibition of heparanase. Roneparstat has shown efficacy in preclinical models of cancers and recently entered Phase I clinical trial in patients with multiple myeloma. Roneparstat markedly decreased the extent of albuminuria and renal damage in mouse models of diabetic nephropathy. This has an important clinical relevance since renal impairment affects between 15-40% of multiple myeloma patients (JCO 2010; 28: 4976).

DESCRIPTION OF THE INVENTION

It has now unexpectedly been found that the combined use of roneparstat with a proteasome inhibitor, preferably selected between bortezomib and carfilzomib, or with melphalan improve efficacy, especially showing synergism, in decreasing the overall tumor burden with respect to the administration of each active ingredient alone. Average tumor burden was determined from the levels of human immunoglobulin light chain and by luciferase imaging.

It is therefore one object of the present invention roneparstat for use in combined therapy with a proteasome inhibitor or with melphalan or a pharmaceutically acceptable salt, hydrate or solvate thereof for the treatment of multiple myeloma, plasma cell myeloma or relapsed refractory myeloma.

It is another object of the present invention a kit-of-part comprising the following components:
 a) Roneparstat;
 b) melphalan or a pharmaceutically acceptable salt thereof, or at least one proteasome inhibitor or a pharmaceutically acceptable salt, hydrate or solvate thereof,
 for use in the prevention or treatment of multiple myeloma.

Another object of the present invention is a pharmaceutical composition comprising Roneparstat and melphalan or at least one proteasome inhibitor or a pharmaceutically acceptable salt, hydrate or solvate thereof, and one or more pharmaceutically acceptable vehicles, excipients or diluents.

Proteasome inhibitors are well-known compounds and their activity can be tested with conventional and commercial assays, as provided for example by Sigma-Aldrich, Abcam, Promega and other commercial providers.

An exemplary list of proteasome inhibitors is shown below:

Proteasome Inhibitors by Chemical Class

β-Lactam

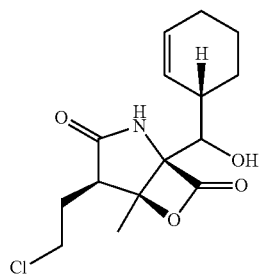

Salinosporamide A

| Proteasome Inhibitors by Chemical Class |
|---|
| 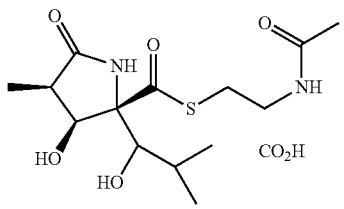 |
| Lactacystin |
| Boronate |
| 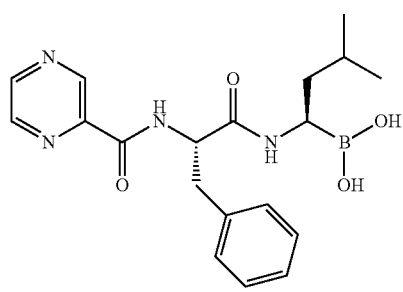 |
| Bortezomib (Velcade) |
| 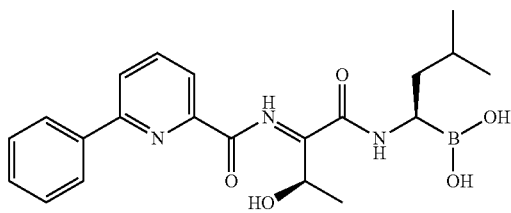 |
| CEP-18770 |
| 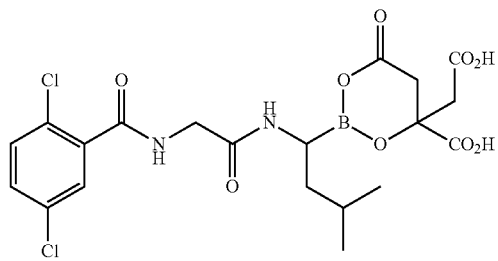 |
| MLN9708 |
| 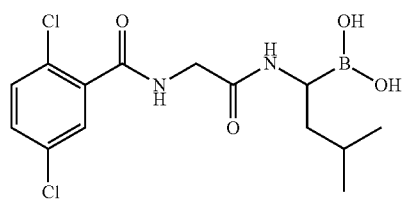 |
| MLN2238 |

-continued
| Proteasome Inhibitors by Chemical Class |
|---|
| Epoxyketone |
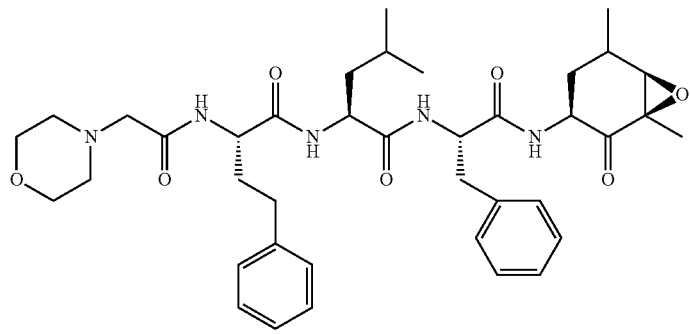
Carfilzomib
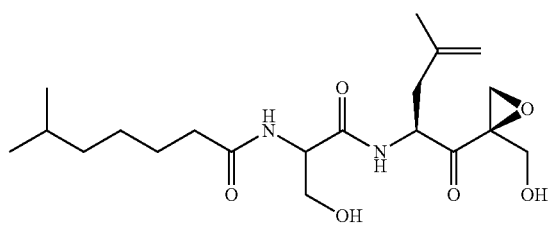
Eponemycin
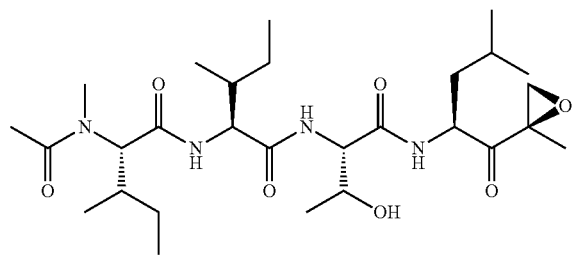
Epoxomicin
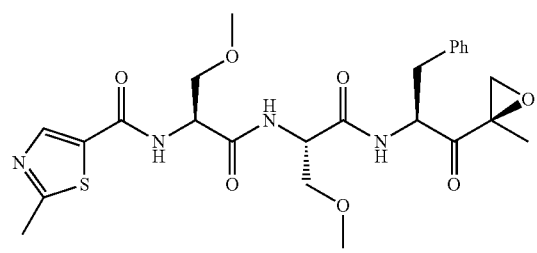
ONX0912

| Proteasome Inhibitors by Chemical Class |
|---|
| Peptide amide |

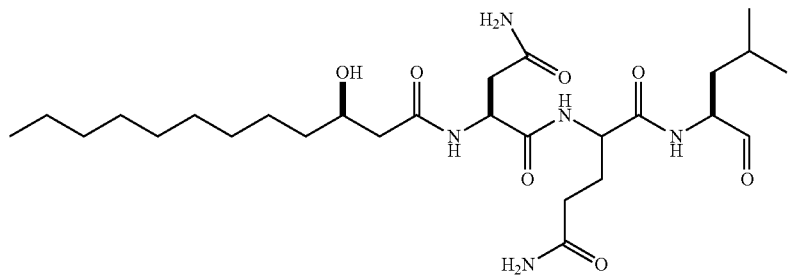

Fellutamide B

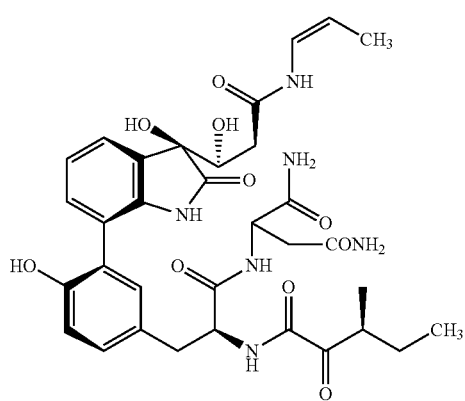

TMC-95A

In a preferred embodiment, the proteasome inhibitor is selected from the group consisting of bortezomid and carfilzomid.

The above-mentioned active ingredients according to the present invention can be administrated in a co-ordinated or combined manner.

What is meant by combined use of the aforesaid compounds is, indifferently, either the co-administration, i.e. the substantially concomitant or sequential supplementation, or the administration of a composition comprising the aforesaid active ingredients in combination and in a mixture optionally further comprising one or more excipients or diluents pharmaceutically acceptable.

The instant invention encompasses methods of treating, inhibiting, and/or preventing multiple myeloma at any stage, plasma cells myeloma, recurrent myeloma or relapsed myeloma or any diseases or disorders associated with multiple myeloma. The methods of the instant invention comprise administering roneparstat in combination with a proteasome inhibitor, preferably bortezomib or carfilzomib, or with melphalan to a subject in need thereof.

The active substances described in the present invention, or a pharmaceutically acceptable salts thereof, may also be used in form of a hydrate or include other solvents used for crystallization, also known as solvates.

What is meant by pharmaceutically acceptable salt of compound described in the present invention is any salt of the latter with an acid that does not give rise to toxic or side effects.

Non-limiting examples of such salts are: chloride, bromide, orotate, aspartate, acid aspartate, acid citrate, magnesium citrate, phosphate, acid phosphate, fumarate and acid fumarate, magnesium fumarate, lactate, maleate and acid maleate, oxalate, acid oxalate, pamoate, acid pamoate, sulphate, acid sulphate, glucose phosphate, tartrate and acid tartrate, glycerophosphate, mucate, magnesium tartrate, 2-amino-ethanesulphonate, magnesium 2-amino-ethanesulphonate, methanesulphonate, choline tartrate, trichloroacetate, and trifluoroacetate.

A list of FDA-approved pharmaceutically acceptable salts is given in the publication Int. J. of Pharm. 33 (1986), 201-217.

The pharmaceutical composition according to the present invention may contain suitable pharmaceutical acceptable carriers, biologically compatible vehicles suitable for administration to an animal (for example, physiological saline) and eventually comprising auxiliaries (like excipients, stabilizers or diluents) which facilitate the processing of the active compounds into preparations which can be used pharmaceutical.

The pharmaceutical composition according to the present invention may be formulated in any acceptable way to meet the needs of the mode of administration. The use of biomaterials and other polymers for drug delivery, as well the different techniques and models to validate a specific mode of administration, are disclosed in literature.

Any accepted mode of administration can be used and determined by those skilled in the art. For example, administration may be by various parenteral routes such as subcutaneous, intravenous, intradermal, intramuscular, intraperitoneal, intranasal, transdermal, oral, or buccal routes.

Bortezomib is generally administered intravenously or subcutaneously. Carfilzominb is generally administered intravenously. Melphalan is generally administered orally or intravenously. Roneparstat is generally administered subcutaneously. "Therapeutically effective amount" is an amount effective to achieve the medically desirable result in the treated subject.

Roneparstat (INN) (previously also designated as [100]NA.ROH or SST0001 or G4000) is a modified heparin derivative that is 100% N-desulphated, N-reacetylated and glycol split. These modifications abolish any clinically relevant anticoagulant activity, but enhance the inhibition of heparanase. Roneparstat has shown efficacy in preclinical models of cancers and recently entered Phase I clinical trial in patients with multiple myeloma (a liquid tumor) (10, 20, 22).

Roneparstat has the following formula (I):

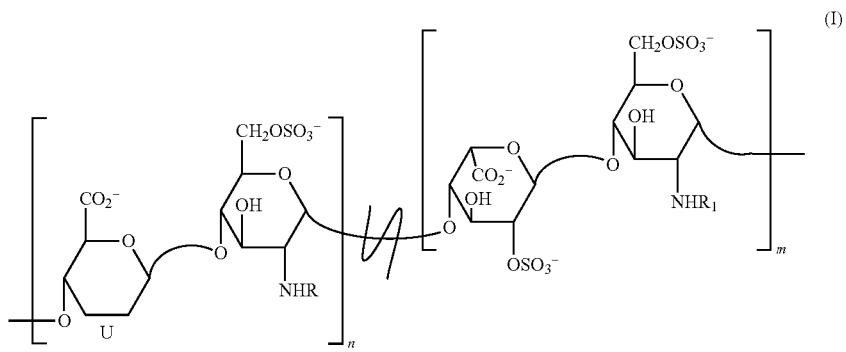

where the U ring is:

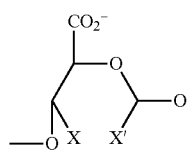

X and X' are the —$CH_2$-D group, where D is hydroxy;
R and $R_1$ are an acetyl residue;
n and m, which can be the same or different, may vary from 1 to 40; the sum of m+n ranges from 6 to 40; the m:n ratio ranges from 10:2 to 1:1,
the symbol indicates that units marked m and n are statistically distributed along the polysaccharide chain and are not necessarily in sequence.

For a complete description of this compound and its manufacturing process, reference can be made to the published patents EP2343077, U.S. Pat. Nos. 7,781,416 and 8,067,555. Reference can also be made to U.S. Pat. No. 8,222,231 and to Ritchie J P, Ramani V C, Ren Y, Naggi A, Torri G, Casu B, et al. SST0001, a chemically modified heparin, inhibits myeloma growth and angiogenesis via disruption of the heparanase/syndecan-1 axis. Clin Cancer Res 2011; 17:1382-93.

Roneparstat preparation has also been described in U.S. Pat. No. 7,781,416 (see [100]NA,RO-H, paragraph bridging columns 24 and 25).

The compounds of the present invention may be prepared from readily available starting materials using the following general methods and procedures. It will be appreciated that where typical or preferred experimental conditions (i.e., reaction temperatures, time, moles of reagents, solvents, etc.) are given, other experimental conditions can also be used unless otherwise stated. Optimum reaction conditions may vary with the particular reactants or solvents used, but such conditions can be determined by one skilled in the art by routine optimisation procedures.

Any of the combination of roneparstat and a proteasome inhibitor, preferably bortezomib or carfilzomib, or melphalan or any bortezomib and/or melphalan or any carfilzomib and/or melphalan containing regimens, the method of treating a warm-blooded animal, preferably a human, comprising administering these two components, a pharmaceutical composition comprising these two components for simultaneous, separate or sequential use, the use of the combination for the delay of progression or the treatment of multiple myeloma or for the manufacture of a pharmaceutical preparation for these purposes or a commercial product comprising such a combination of such components, all as mentioned or defined above, will be referred to subsequently also as combination of the invention (so that this term refers to each of these embodiments which thus can replace this term where appropriate).

Simultaneous administration may, e.g., take place in the form of one fixed combination with two or more active ingredients, or by simultaneously administering two or more active ingredients that are formulated independently. Sequential use (administration) preferably means administration of one (or more) components of a combination at one time point, other components at a different time point, that is, in a chronically staggered manner, preferably such that the combination shows more efficiency than the single compounds administered independently (especially showing synergism). Separate use (administration) preferably means administration of the components of the combination independently of each other at different time points.

Also combinations of two or more of sequential, separate and simultaneous administration are possible, preferably such that the combination component-drugs show a joint therapeutic effect that exceeds the effect found when the combination component-drugs are used independently at time intervals so large that no mutual effect on their therapeutic efficiency can be found, a synergistic effect being especially preferred.

The terms "treatment" or "treating", as used herein, include the concept of delay of progression of the disease or pathology to be treated. According to the present invention, it will refer to inhibition of the tumor cell growth, a reduction of the tumor cell mass, and/or to an inhibition of the production of metastasis.

The term "delay of progression", as used herein, means administration of the combination to patients being in a pre-stage or in an early phase, of the first or subsequent manifestations; or a relapse of the disease to be treated in which patients, e.g., a pre-form of the corresponding disease is diagnosed; or which patients are in such a condition, e.g., during a medical treatment.

In general, the word "prevention" includes a wide range of activities—known as "interventions"—aimed at reducing risks or threats to health. These are usually grouped into three categories. The first is "primary prevention". Here the goal is to protect healthy people from developing a disease or experiencing an injury in the first place, for example routine screening programs to monitor risk factors for illness, immunization against infectious disease, etc.

The second one is the so-called "secondary prevention". These interventions happen after an illness or serious risk factors have already been diagnosed. The goal in this case is to halt or slow the progress of disease (if possible) in its earliest stages.

The third one is the "tertiary prevention". This focuses on helping people manage complicated, long-term health problems, such as cancer. The goals include preventing further physical deterioration and maximizing quality of life. ("At Work", Issue 43, Winter 2006: Institute for Work & Health, Toronto)

According to the present invention, the word prevention is intended to refer more to secondary and tertiary prevention of multiple myeloma.

"Jointly therapeutically active" or "joint therapeutic effect" means that the two components (or active ingredients) may be given separately (in a chronically staggered manner, especially a sequence-specific manner) in such time intervals that they preferably, in the warm-blooded animal, especially human, to be treated, still show a (preferably synergistic) interaction (joint therapeutic effect).

"Therapeutically effective" preferably relates to an amount that is therapeutically or in a broader sense also prophylactically effective against the progression of a proliferative disease. Such amount is found through normal clinical trials, whose design is within the skills of the person of ordinary experience in this field. See also EMA or FDA Guidelines.

The term "a commercial package" or "a product", as used herein defines especially a "kit of parts" in the sense that it contains roneparstat (a) and a proteasome inhibitor or melphalan (b); this implies only 2 component-combinations.

We need to also state that the compounds that can be used in the "combination" as defined above, can be dosed independently or by use of different fixed combinations with distinguished amounts of the components (a) and (b), i.e., simultaneously or at different time points. Moreover, these terms comprise a commercial package comprising (especially combining) as active ingredients components (a) and (b), together with instructions for simultaneous, sequential (chronically staggered, in time-specific sequence, preferentially) or (less preferably) separate use thereof in the delay of progression or treatment of a proliferative disease. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (a) and (b) as can be determined according to standard methods. The ratio of the total amounts of the combination partner (a) to the combination partner (b) to be administered in the combined preparation can be varied, e.g., in order to cope with the needs of a patient sub-population to be treated or the needs of the single patient which different needs can be due to the particular disease, age, sex, body weight, etc. of the patients. Preferably, there is at least one beneficial effect, e.g., a mutual enhancing of the effect of the combination partners (a) and (b), in particular, a more than additive effect, which hence could be achieved with lower doses of each of the combined drugs, respectively, than tolerable in the case of treatment with the individual drugs only without combination, producing additional advantageous effects, e.g., less side effects or a combined therapeutic effect in a non-effective dosage of one or both of the combination partners (components) (a) and (b), and very preferably a strong synergism of the combination partners (a) and (b).

Both in the case of the use of the combination of components (a) and (b) and of the commercial package, any combination of simultaneous, sequential and separate use is also possible, meaning that the components (a) and (b) may be administered at one time point simultaneously, followed by administration of only one component with lower host toxicity either chronically, e.g., more than 3-4 weeks of daily dosing, at a later time point and subsequently the other component or the combination of both components at a still later time point (in subsequent drug combination treatment courses for an optimal anti-tumor effect) or the like.

The kit-of parts of the present invention can be marketed also in the form where component a) (i.e. Roneparstat) and component b) (i.e. the proteasome inhibitor or melphalan) can be separately packaged. The combination of the invention can also be applied in combination with other treatments, e.g., surgical intervention, hyperthermia and/or irradiation therapy.

The combination of the invention will generally be administered in a suitable formulation. Such formulation takes the form of conventional pharmaceutical compositions.

The therapy can be combined with other known chemotherapies, radiotherapies or hormonal therapies, if desired for added clinical effectiveness.

Hence, pharmaceutical compositions comprising roneparstat and a pharmaceutically acceptable carrier, diluent or excipient therefore is also within the scope of the present invention. Such compositions can be prepared in a manner well known in the pharmaceutical art and comprise at least one active compound. A person skilled in the art is aware of a whole variety of such carrier, diluent or excipient compounds suitable to formulate a pharmaceutical composition.

Roneparstat together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Generally, each active ingredient is administered in a "pharmaceutically effective amount". The amount of the compound actually administered will typically be determined by a physician, in the light of the relevant circumstances, including the condition to be treated, the chosen route of administration, the actual compound administered, drug combination, the age, body weight, and response of the individual patient, the severity of the patient's symptoms, and the like. Generally, an effective dose will be from 0.01 mg/kg to 100 mg/kg, preferably 0.05 mg/kg to 50 mg/kg. Compositions may be administered individually to a patient or may be administered in combination with other agents, drugs, hormones, irradiation or surgery. For any compound, the therapeutically effective dose can be estimated initially either in cell culture assays or in animal models, usually mice, rats, guinea pigs, rabbits, dogs, monkeys or pigs.

The animal model may also be used to determine the appropriate concentration range and route of administration. Such information can then be used to determine useful doses and routes for administration in humans. In calculating the Human Equivalent Dose (HED) it is recommended to use the conversion table provided by the FDA in Guidance for Industry and Reviewers document available from FDA. The pharmaceutical compositions of the invention can be administered by a variety of routes including oral, rectal, sublingual, transdermal, subcutaneous, intravenous, intramuscular, intrathecal, intraperitoneal, intranasal and locally on the diseased tissue after surgical operation.

The dose and mode of administration as well as the therapeutic posology will be determined by the physician according to his experience, severity of the disease, conditions of the patient and any other consideration pertaining to medical profession.

In an embodiment of the present invention, Bortezomib is administered to patients in need thereof at doses commonly used in the clinical practice. For example two open-label, phase II trials (SUMMIT and CREST) established the efficacy of bortezomib 1.3 mg/m$^2$ administered by intravenous bolus on days 1, 4, 8 and 11 of a 21-day cycle for a maximum of eight cycles.

In an embodiment of the present invention, Carfilzomib is administered to patients in need thereof at doses commonly used in the clinical practice. For example Cycle 1 dose is 20 mg/m$^2$/day and if tolerated increase Cycle 2 dose and subsequent cycles doses to 27 mg/m$^2$/day. It may be administered intravenously over 2 to 10 minutes, on two consecutive days each week for three weeks (Days 1, 2, 8, 9, 15, and 16), followed by a 12-day rest period (Days 17 to 28).

In an embodiment of the present invention, Melphalan is administered to patients in need thereof at doses commonly used in the clinical practice, for example at an intravenous dose: 16 mg/m$^2$. The drug is administered as a single infusion over 15 to 20 minutes. Melphalan is administered at two week intervals for four doses, then, after adequate recovery from toxicity, at four week intervals.

The most usual oral dose for melphalan is 6 mg once a day. After 2 to 3 weeks of treatment, a maintenance dose of 2 mg daily may be instituted.

Roneparstat is administered to patients in need thereof at doses suggested by the physicians in the clinical practice. For example suitable subcutaneous doses are comprised between 100 and 600 mg per day, preferably between 200 and 400 mg per day.

Depending on the intended route of delivery, roneparstat is preferably formulated as parenteral, topical or oral compositions. The compositions for oral administration may take the form of bulk liquid solutions or suspensions, or bulk powders. More commonly, however, the compositions are presented in unit dosage forms to facilitate accurate dosing.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include refilled, pre-measured ampoules or syringes of the liquid compositions or pills, tablets, capsules or the like in the case of solid compositions. In such compositions, the compound of the invention can be a minor or major component with the remainder being various vehicles or carriers and processing aids helpful for forming the desired dosing form. In the case of a lyophilized composition for injection roneparstat is generally present as a major component of the composition (80-100% by weight). When reconstituted with water for injectable roneparstat is generally at a concentration of from 50 to 200 mg/ml.

Dosage treatment may be a single dose schedule or a multiple dose schedule Liquid forms suitable for oral administration may include a suitable aqueous or non-aqueous vehicle with buffers, suspending and dispensing agents, colorants, flavors and the like.

Solid forms may include, for example, any of the following ingredients, or compounds of a similar nature: a binder such as microcrystalline cellulose, acacia, gum tragacanth, gelatine or polyvinyl-pyrrolidone; an excipient such as starch or lactose, a disintegrating agent such as alginic acid, Primogel, or potato or corn starch; a lubricant such as magnesium stearate, talc, polyethylene glycol or silica; a glidant such as colloidal silicon dioxide; a sweetening agent such as sucrose or saccharin; or a flavoring agent such as pepper-mint, methyl salicylate, or orange flavoring. The tablets may be coated according to methods well known from people skilled in the art of pharmaceutical practice.

Parenteral compositions are typically based upon injectable sterile saline or phosphate-buffered saline or other injectable carriers known in the art. Roneparstat can also be administered in sustained release forms or from sustained release drug delivery systems.

A description of representative sustained release materials as well as further materials and processing techniques are set out in Part 5 of Remington's Pharmaceutical Sciences, 20th Edition, 2000, Merck Publishing Company, Easton, Pa.

Usually medical doctors describe a cancer's growth or spread. This is called the stage of the disease. For multiple myeloma a classification system called International Staging System (ISS) is now used more commonly. It defines the factors that influence patient survival. The ISS is based on data collected from patients with multiple myeloma from around the world. The system has three stages based on the measurement of serum albumin and the levels of serum P2 microglobulin, as follows:

Stage I: β2-M less than 3.5 mg/L and albumin greater than or equal to 3.5 gm/dL.

Stage II: Either β2-M greater than 3.5 mg/L but not greater than 5.5 mg/dL and/or albumin less than 3.5 g/dL.

Stage III: β2-M greater than 5.5 mg/L.

Myeloma that returns after a period of being in control after treatment is called recurrent myeloma or relapsed myeloma. If there is a recurrence, the cancer may need to be staged again (called re-staging).

According to the 2008 WHO classification of lymphoid neoplasms, plasma cell myeloma (multiple myeloma) is also classified, as asymptomatic (smoldering) or symptomatic myeloma, depending on the absence or presence of myeloma-related organ or tissue dysfunction (Campo E. et al., Blood 2011; 117: 5019-5032).

Plasma cell neoplasms have proven challenging to be classified in a biologically correct and clinically useful way. Because the immunoglobulin products of plasma cells are easily detected in the serum and urine, evidence of small clones of plasma cells may be detected by routine laboratory tests in patients who are healthy and may never develop organ damage secondary to the clonal proliferation. In addition, deposition of abnormal secreted immunoglobulin heavy or light chains or both (eg, amyloidosis) in tissues may occur in the presence of a very small plasma cell clone, with organ damage that is because of the deposits, not related to the plasma cell burden. The definition of plasma cell myeloma (PCM) has rested on identifying clinical and laboratory features that predict when a sufficient burden of plasma cells has accumulated so that the patient will benefit from treatment.

The diagnosis of PCM, in the absence of myeloma-related end-organ damage (hypercalcemia, renal failure, anemia, bone lesions), requires the presence of a serum M-protein of 30 g/L and/or 10% bone marrow clonal plasma cells, so-called asymptomatic (smoldering) myeloma. Cases not meeting these criteria are considered monoclonal gammopathy of undetermined significance (MGUS).

In contrast, if myeloma-related end-organ damage is present, PCM is diagnosed when one detects an M-protein in the serum or urine of any amount and any number of bone marrow clonal plasma cells (usually exceeding 10% of all cells) or plasmacytoma (Campo E. et al., Blood 2011; 117: 5019-5032).

The combined treatment of the present invention is suitable for the treatment of any of the previously described stages of multiple myeloma patients, according to the doctors' determination and prescription.

In the following the present invention shall be illustrated by means of some Examples which are not construed to be viewed as limiting the scope of the invention.

The Examples will make reference to the following Figures or Drawings.

EXAMPLES

Example 1—Roneparstat with Bortezomib

Experimental Design

Figure 1:
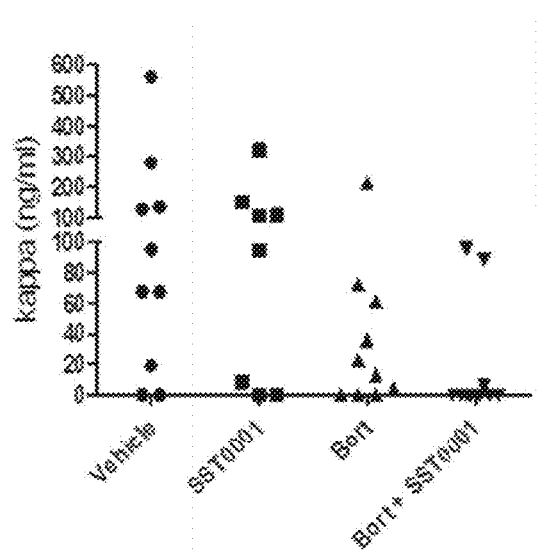
FIG. 1. It reports the results coming from the roneparstat (SST0001) in vivo combination studies with bortezomib. Animals were injected with CAG HPSE cells; after 7 days animals were divided into four groups and treated for two additional weeks with a) vehicle, b) bortezomib (at a dose 0.5 mg/kg/twice a week intraperitoneally, c) roneparstat (at a dose of 120 mg/kg/day subcutaneously) or a combination of (b) and (c).

All the experiments were done using an experimental metastasis model of myeloma. For this model, three million human myeloma cells expressing high levels of heparanase were injected intravenously into the lateral tail vein of SCID mice. These cells home to and grow predominantly within the mouse bone and thus this model closely replicates the disseminated myeloma disease seen in humans. Development of the disease is tracked in real time by bioluminescence imaging of the luciferase labeled tumor cells. This model was utilized to establish whether roneparstat in combination with bortezomib could overcome chemoresistance of CAG HPSE high cells and enhance the tumor cell killing of bortezomib.

CAG human myeloma cell line was established at the Myeloma Institute for Research and Therapy (Little Rock, Ark.). CAG cells with modified levels of heparanase expression have been extensively characterized and include (a) heparanase-low (HPSE-low) cells prepared by transfection with empty vector; and (b) heparanase-high (HPSE-high) cells prepared by transfection with vector containing the cDNA for human heparanase. Although HPSE-high cells express a 4-fold higher level of heparanase than do the HPSE-low cells, the elevated levels of enzyme activity present in HPSE-high cells are in the same range as that present in the bone marrow of many myeloma patients (Kelly T. et al, Cancer Res 2003; 63:8749-56). This indicates that HPSE-high cells very closely mimic the level of heparanase activity present in many myeloma patients and thus represent an appropriate model for examining the effects of heparanase on myeloma tumors. The preparation of the CAG-HPSE high cells is described in Yang Y, et al, The Journal Of Biological Chemistry, Vol. 282, No. 18, pp. 13326-13333, May 4, 2007 (see in particular page 13327, left column, the paragraph beginning with "For transfections . . . ").

Treatment Schedule 7 days post intravenous injection of CAG HPSE high cells, the animals were then divided into four separate groups and treated with a) vehicle, or b) roneparstat (120 mg/kg/day) delivered subcutaneously, or c) bortezomib (0.5 mg/kg/twice a week) delivered intraperitoneally, or d) both roneparstat and bortezomib for the next two weeks. After two weeks of treatment (Day 21) serum was harvested. (Number of animals used=40).

Analysis a. Tumor growth and size was monitored weekly by bioluminescence. At the completion of the experiment, the intensity of lumniscent images (both dorsal and ventral) from all the experimental groups was quantified using Living Image® software (by Perkin Elmer). Bioluminescent data from individual animals is presented as total flux and as total counts.

b. enzyme-linked immunosorbent assays (ELISA) for human immunoglobulin light chain levels in mouse serum as an indicator of whole animal tumor burden.

c. Whole body weight of animals was recorded weekly after the injection of tumor cells.

Material

Roneparstat was provided by Sigma-Tau Research S.A.; as vehicle, phosphate buffered saline (PBS) was used.

Bortezomib was used as PS-341(Velcade®); reconstituted in dimethyl sulfoxide; as vehicle, PBS was used.

Animals

Species, Strain, Number, Sex and Age

Mouse, CB. 17/Icr SCID, male, 10 animals per group, male, 6-8 weeks, by Charles River.

Animal Husbandry

Mice were housed inside microisolator cages following standard for immunocompromised mice. Mice were maintained in cages with paper filter covers; food and bedding are sterilized and water is acidified. Animals were housed under a light-dark cycle, keeping temperature and humidity.

Identification of Animals and Allocation to Groups

Animals were subdivided into the different dosage groups. Each cage was identified by a paper tag indicating: number of mice, name of the test item, dose and route of administration, type of cells injected, date of tumor injection and number of group. At the end of the experiments animals were subjected to mild anesthesia and euthanized by cervical dislocation.

Results and Conclusions

The heparin derivative roneparstat, improved the efficacy of bortezomib in decreasing the overall tumor burden, especially showing synergism. Average tumor burden as determined from the levels of human immunoglobulin light chain and by luciferase imaging revealed the lowest tumor burden in animals treated with the combination of both roneparstat and bortezomib. Further, only 3/10 animals in the combination therapy group had detectable tumor burden (data are not shown here, but are available upon request), whereas 8/10 animals receiving either PBS or bortezomib alone and 6/8 animals receiving roneparstat alone had detectable levels of human immunoglobulin light chain.

This was evident both from kappa-levels and luminescence imaging data; a decrease in the former was always paralleled by a decrease of the latter (see Table 1 and FIG. 1).

TABLE 1

Roneparstat in vivo combination studies with bortezomib

| Group of treatment | % of animals with kappa levels (above detection limit) |
| --- | --- |
| Vehicle | 80% |
| Roneparstat | 70% |
| Bortezomib | 75% |
| Roneparstat + Bortezomib | 30%* |

*Only 3/10 animals had detectable levels of serum kappa in the combined treatment group.

Example 2—Roneparstat with Melphalan

Experimental Design

All the experiments were done using the same experimental model reported in Example 1 here to establish whether roneparstat in combination with melphalan could overcome chemoresistance of CAG HPSE high cells.

Treatment Schedule 7 days post i.v. injection of CAG HPSE high cells, the animals were then divided into four separate groups and treated with a) vehicle, or b) roneparstat (60 mg/kg/day) delivered subcutaneously, or c) melphalan (1 mg/kg/week) delivered i.p., or d) both roneparstat and melphalan for the next two weeks. After two weeks of treatment (Day 21) serum was harvested. (Number of animals used=40).

Analysis

Same as in Example 1.

Material

Roneparstat was provided by Sigma-Tau Research S.A.; as vehicle, phosphate buffered saline (PBS) was used.

Melphalan was purchased from Sigma-Aldrich (Catalog # M2011 Lot #063M4122V).

Animals

Species, Strain, Number, Sex and Age

Mouse, CB. 17/Icr SCID, male, 10 animals per group, male, 6-8 weeks, by Charles River.

Animal Husbandry

Same as in Example 1

Identification of Animals and Allocation to Groups

Same as in Example 1.

Results and Conclusions

Figure 2:
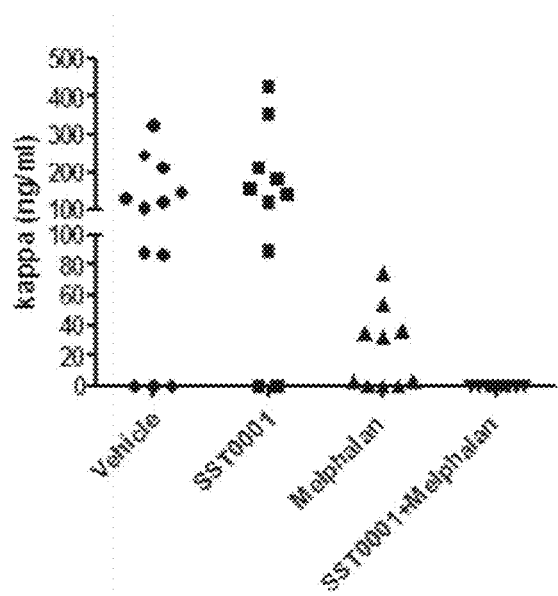
FIG. 2. It reports the results coming from the roneparstat (SST0001) in vivo combination studies with melphalan. Animals were injected with CAG HPSE cells; after 7 days animals were divided into four groups and treated for two additional weeks with a) vehicle, b) melphalan (at a dose 1.0 mg/kg/week intraperitoneally), c) roneparstat at a dose of 60 mg/kg/day subcutaneously) or a combination of (b) and (c).

The heparin derivative roneparstat, improved the efficacy of melphalan in decreasing the overall tumor burden, especially showing synergism. Average tumor burden as determined from the levels of human immunoglobulin light chain and by luciferase imaging revealed the lowest tumor burden in animals treated with the combination of both roneparstat and melphalan. Surprisingly no animal in the combination treatment group had detectable tumor burden, whereas 9/12 animals receiving PBS, 8/9 animals receiving roneparstat alone and 7/10 animals receiving melphalan alone had detectable levels of human immunoglobulin light chain (see Table 2 and FIG. 2).

TABLE 2

Roneparstat in vivo combination studies with melphalan

| Group of treatment | % of animals with kappa levels (above detection limit) |
| --- | --- |
| Vehicle | 75% |
| Roneparstat | 89% |
| Melphalan | 70% |
| Roneparstat + Melphalan | 0 |

Example 3—Roneparstat with Melphalan—Maintenance Therapy

Experimental Design

All the experiments were done using the same experimental model reported in Example 1 here to establish whether roneparstat in combination with melphalan could overcome chemoresistance of CAG HPSE high cells.

Treatment Schedule 7 days post intravenous injection of CAG HPSE high cells, the animals were then divided into three separate groups (of 11 animals each) and treated as follows:

Group A—Animals were treated with combination of melphalan (2.5 mg/kg/week) and roneparstat (60 mg/kg/day) for two weeks. The animals were then left untreated for two additional weeks;

Group B—Animals were treated with melphalan (2.5 mg/kg/week) for first two weeks followed by daily injections of PBS for two additional weeks; and Group C—Animals were treated with melphalan (2.5 mg/kg/week) for two weeks followed by daily injections of roneparstat (120 mg/kg/day) for additional two weeks (Note—in this group one animal died at the 32$^{nd}$ day of treatment. Therefore we switched to 60 mg/kg/day roneparstat dose for the last 3 days of the treatment period).

Total duration of experiment was 5 weeks. After 5 weeks of treatment (Day 35) serum was harvested. Number of animals used was 33.

Analysis

Same as in Example 1.

Material

Same as in Example 2.

Animals

Species, Strain, Number, Sex and Age

Mouse, CB. 17/Icr SCID, male, 11 animals per group, male, 6-8 weeks, by Charles River.

Animal Husbandry

Same as in Example 1.

Identification of Animals and Allocation to Groups

Same as in Example 1.

Results and Conclusions

Figure 3:
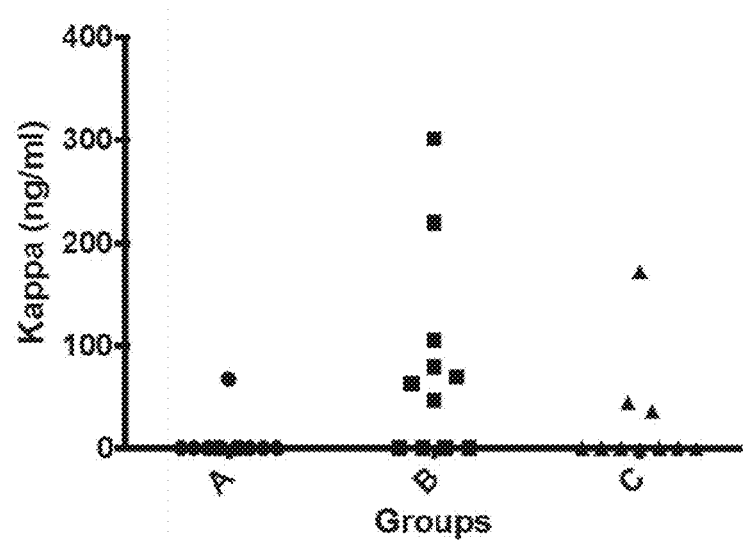
FIG. 3. It reports the results coming from the roneparstat (SST0001) in vivo combination studies with melphalan. Duration of the experiment was five weeks. Animals were injected with CAG HPSE cells; after 7 days animals were divided into three groups and treated for two additional weeks with (a) a combination of melphalan (at a dose at a dose of 2.5 mg/kg/week intraperitoneally) and roneparstat (at a dose of 60 mg/kg/day subcutaneously) and left untreated for the remaining two weeks, (b) melphalan alone (at a dose at a dose of 2.5 mg/kg/week intraperitoneally) and PBS for the remaining two weeks, or (c) melphalan alone (at a dose at a dose of 2.5 mg/kg/week intraperitoneally) and subsequently roneparstat (at a dose of 60 mg/kg/day subcutaneously) for the remaining two weeks.

In animals treated with the combination of SST0001 and melphalan, only 1/11 animals had detectable tumor burden when tested two weeks after the end of therapy. After initial melphalan treatment, in animals that received SST0001 for the next two weeks only 3/10 animals had detectable tumor burden whereas 7/11 animals that received PBS displayed detectable tumor burden. Use of SST0001 either alongside or after chemotherapy clearly affects tumor burden (see Table 3 and FIG. 3).

TABLE 3

Roneparstat with melphalan - Maintenance therapy

| Groups | Average Kappa ± SEM (ng/ml) | Animals with detectable levels of Kappa |
|---|---|---|
| A | 6.163 ± 6.163 | 1 out of 11 |
| B | 80.59 ± 29.60 | 7 out of 11 |
| C | 25.35 ± 17.15 | 3 out of 10 |

Example 4—Roneparstat with Carfilzomib

Experimental Design

HPSE-high cells were seeded in serum free media overnight and then treated with 6.75 µM roneparstat (Rone) for 6 hours, washed and then treated with carfilzomib (CFZ) (15 nM) for 14 hours and viability was assessed by MTT assay. The MTT assay is a colorimetric assay for assessing cell viability, which takes its name from tetrazolium dye MTT (3-(4,5-dimethylthiazol-2-yl)-2,5-diphenyltetrazolium bromide). Under certain conditions the cellular oxidoreductase enzymes reduce MTT to its insoluble formazan, which has a purple color.

Material

Roneparstat was provided by Sigma-Tau Research S.A.; as vehicle, phosphate buffered saline (PBS) was used.

Carfilzomib was purchased from (Selleckchem, Houston, Tex., USA).

Results and Conclusions

Figure 4:
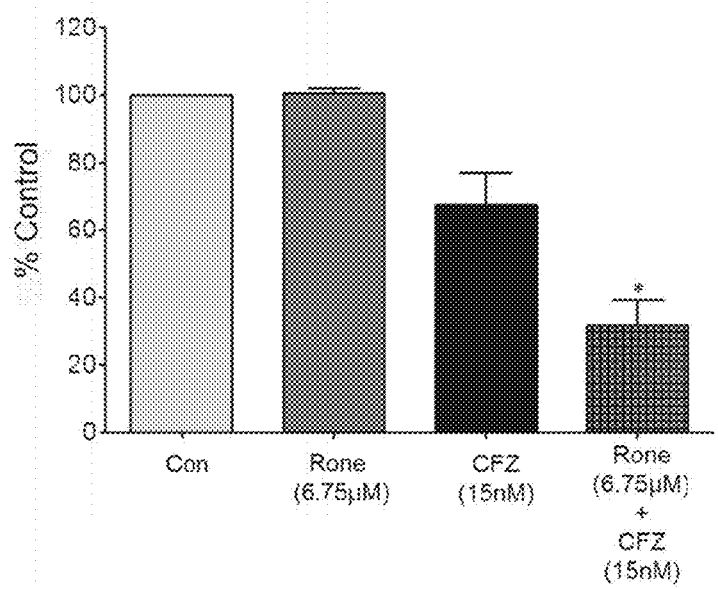
FIG. 4: it reports the viability of HPSE-high cells untreated, treated with roneparstat (Rone) alone, with carfilzomib (CFZ) alone or with a combination of roneparstat and carfilzomib; cell viability was assessed by MTT assay.

The heparin derivative roneparstat improved the efficacy of carfilzomib in decreasing the viability of the myeloma cells tested, especially showing synergism. In particular a significant result was obtained, about 35% of the myeloma cells showing survival after the combined treatment (see FIG. 4), while neither roneparstat or carfilzomib provided significant results when administered alone.

The invention claimed is:

1. A method for treating or preventing a multiple myeloma in an individual in need thereof, comprising administering to the individual in need thereof a combined therapy comprising:
   (a) a roneparstat, or a pharmaceutically acceptable salt, hydrate or solvate thereof, and;
   (b) (i) a melphalan or a pharmaceutically acceptable salt, hydrate or solvate thereof, (ii) a proteasome inhibitor, or (iii) a combination thereof,
   wherein said component (a) and said component (b) are separately or sequentially administered at an effective amount that is determined by synergistic reduction of immunoglobulin light chain kappa level.

2. The method of claim 1, wherein said proteasome inhibitor comprises: a bortezomib or a pharmaceutically acceptable salt, hydrate or solvate thereof; a carfilzomib or a pharmaceutically acceptable salt, hydrate or solvate thereof; or, a combination thereof.

3. The method of claim 1, wherein the multiple myeloma is at any stage, or is a recurrent, refractory or relapsed myeloma.

4. The method of claim 1, wherein the roneparstat is administered in a subcutaneous dose of from about 100 to about 600 mg daily.

5. The method of claim 1, wherein said proteasome inhibitor for the combined therapy comprises a bortezomib administered in a dose of about 1.3 mg/m$^2$ by intravenous bolus, optionally on days 1, 4, 8 and 11, or optionally at a 21-day cycle for a maximum of eight cycles.

6. The method of claim 1, wherein said proteasome inhibitor for the combined therapy is carfilzomib and it is administered intravenously in a dose of 20 mg/m$^2$/day, optionally on two consecutive days each week for three weeks.

7. The method of claim 1, wherein for the combined therapy the melphalan is administered intravenously in a dose of about 16 mg/m$^2$, optionally as a single infusion over 15 to 20 minutes.

8. The method of claim 1, wherein for the combined therapy the melphalan is administered in an oral dose of about 6 mg once a day for 2 to 3 weeks.

9. A method of treating a human suffering from multiple myeloma, plasma cell myeloma, or recurrent, refractory or relapsed myeloma comprising administering to the human in need thereof a therapeutically effective amount of a pharmaceutical composition or a therapeutic combination comprising:
   (a) a roneparstat, or a pharmaceutically acceptable salt, hydrate or solvate thereof, and;
   (b) (i) a melphalan or a pharmaceutically acceptable salt, hydrate or solvate thereof, (ii) a proteasome inhibitor, or (iii) a combination thereof, wherein said component (a) and said component (b) are separately or sequentially administered at the effective amount that is determined by synergistic reduction of immunoglobulin light chain kappa level.

10. A method for inhibiting, treating, or preventing multiple myeloma, plasma cell myeloma, or recurrent, refractory or relapsed myeloma in a subject, said method comprising administering to the subject in need thereof a therapeutically effective amount of a pharmaceutical composition or a therapeutic combination comprising:
(a) a roneparstat, or a pharmaceutically acceptable salt, hydrate or solvate thereof, and;
(b) (i) a melphalan or a pharmaceutically acceptable salt, hydrate or solvate thereof, (ii) a proteasome inhibitor, or (iii) a combination thereof,
wherein said component (a) and said component (b) are separately or sequentially administered at the effective amount that is determined by synergistic reduction of immunoglobulin light chain kappa level.

11. The method of claim 1, wherein said component (a) and said component (b) are formulated independently.

12. The method of claim 1, wherein said component (a) and said component (b) are separately packaged.

13. The method of claim 1, wherein said component (a) and said component (b) are packaged or formulated together.

14. The method of claim 9, wherein the proteasome inhibitor comprises: a bortezomib or a pharmaceutically acceptable salt, hydrate or solvate thereof; a carfilzomib or a pharmaceutically acceptable salt, hydrate or solvate thereof; or, a combination thereof.

15. The method of claim 10, wherein the proteasome inhibitor comprises: a bortezomib or a pharmaceutically acceptable salt, hydrate or solvate thereof; a carfilzomib or a pharmaceutically acceptable salt, hydrate or solvate thereof; or, a combination thereof.

16. The method of claim 9, wherein the roneparstat is administered in a subcutaneous dose of from between about 100 to about 600 mg daily.

17. The method of claim 10, wherein the roneparstat is administered in a subcutaneous dose of from about 100 to about 600 mg daily.

18. The method of claim 1, wherein the combined therapy comprises:
(a) a roneparstat, or a pharmaceutically acceptable salt, hydrate or solvate thereof, and;
(b) a melphalan or a pharmaceutically acceptable salt, hydrate or solvate thereof.

19. The method of claim 1, wherein the combined therapy comprises:
(a) a roneparstat, or a pharmaceutically acceptable salt, hydrate or solvate thereof, and;
(b) a proteasome inhibitor.

20. The method of claim 19, wherein the proteasome inhibitor comprises bortezomib.

21. The method of claim 19, wherein the proteasome inhibitor comprises carfilzomib.

22. The method of claim 1, wherein the combined therapy comprises:
(a) a roneparstat, or a pharmaceutically acceptable salt, hydrate or solvate thereof, and;
(b) (i) a melphalan or a pharmaceutically acceptable salt, hydrate or solvate thereof, and (ii) a proteasome inhibitor.

* * * * *